US011246393B2

(12) United States Patent
Brugger et al.

(10) Patent No.: US 11,246,393 B2
(45) Date of Patent: Feb. 15, 2022

(54) DISPENSING CONTAINER

(71) Applicants: Gerhard Brugger, Pflach (AT); EMPHASYS IMPORT ADORA EXPORTADORE E DISTRIBUIDORA LTDA., Porto Feliz SP (BR)

(72) Inventors: Gerhard Brugger, Pflach (AT); Victor Esteve, Itú (BR)

(73) Assignees: Gerhard Brugger, Pflach (AT); Emphasys Importadora Exportadora e Distribuidora Ltda., Porto Feliz SP (BR)

( * ) Notice: Subject to any disclaimer, the term of this patent is extended or adjusted under 35 U.S.C. 154(b) by 173 days.

(21) Appl. No.: 16/626,653

(22) PCT Filed: Jun. 27, 2017

(86) PCT No.: PCT/EP2017/065791
§ 371 (c)(1),
(2) Date: Dec. 26, 2019

(87) PCT Pub. No.: WO2019/001687
PCT Pub. Date: Jan. 3, 2019

(65) Prior Publication Data
US 2020/0148462 A1 May 14, 2020

(51) Int. Cl.
*A45D 34/04* (2006.01)
*B65D 83/64* (2006.01)
(Continued)

(52) U.S. Cl.
CPC .......... *A45D 34/04* (2013.01); *B65D 83/0011* (2013.01); *B65D 83/64* (2013.01);
(Continued)

(58) Field of Classification Search
CPC ............ B65D 83/0005; B65D 83/0011; B65D 83/0022; A45D 33/18; A45D 33/04;
(Continued)

(56) References Cited

U.S. PATENT DOCUMENTS 1,235,351 A * 7/1917 McLaughlin ...... B65D 83/0005
222/387
1,263,908 A * 4/1918 Loeben .............. B65D 83/0005
222/387
(Continued)

FOREIGN PATENT DOCUMENTS

EP 2 123 188 A1 11/2009
JP 2008-289849 A 12/2008
(Continued)

OTHER PUBLICATIONS

English Language Abstract of JP2008289849A.
English Language Abstract of JP2011050412A.

*Primary Examiner* — Patrick M. Buechner
(74) *Attorney, Agent, or Firm* — Ware, Fressola, Maguire & Barber LLP

(57) ABSTRACT

A dispensing container for viscous products features a cream pot having an inner cylinder defining a storage volume to store a viscous product; a cap closes the cream pot and has a dispensing outlet; a screw rod rotatably connects to the cream pot; a piston having an inner thread couples to the screw rod so rotation of the screw rod moves of the piston in the inner cylinder along a longitudinal axis of the screw rod to reduce the storage volume of the inner cylinder and dispense the product through the dispensing outlet; an indexing mechanism locks the screw rod in rotational positions with respect to the cream pot and has indexing spring elements located at the screw rod and indexing sections located at a bottom of the cream pot, the indexing spring
(Continued)

elements interact with the indexing sections to lock the screw rod with respect to the cream pot.

19 Claims, 12 Drawing Sheets

(51) Int. Cl.
*A45D 40/04* (2006.01)
*B65D 83/00* (2006.01)
*A45D 40/00* (2006.01)

(52) U.S. Cl.
CPC .......... *A45D 40/0075* (2013.01); *A45D 40/04* (2013.01); *A45D 2200/055* (2013.01); *B65D 83/0022* (2013.01)

(58) Field of Classification Search
CPC ........ A45D 2040/0012; A45D 40/0068; A45D 40/0075; A45D 40/04; A45D 2200/055; A45D 2200/054; A45D 2200/05; G01F 11/024; G01F 11/025; G01F 11/32; G01F 11/34; A61M 35/003
See application file for complete search history.

(56) References Cited

U.S. PATENT DOCUMENTS

| | | | |
|---|---|---|---|
| 1,950,324 A * | 3/1934 | Powers | A45D 40/04 401/194 |
| 4,850,516 A * | 7/1989 | Seager | B65D 83/0011 222/390 |
| 5,000,356 A | 3/1991 | Johnson et al. | |
| 5,573,341 A * | 11/1996 | Iaia | A45D 40/04 401/172 |
| 5,725,133 A * | 3/1998 | Iaia | A45D 40/04 222/390 |
| 6,269,982 B1 * | 8/2001 | Kreiseder | A45D 40/04 222/326 |
| 2005/0242127 A1 * | 11/2005 | Bougamont | B65D 83/0027 222/390 |
| 2007/0025799 A1 * | 2/2007 | Crosnier | A45D 40/04 401/66 |
| 2008/0078846 A1 * | 4/2008 | Tsai | B05B 11/3098 239/333 |
| 2011/0020048 A1 * | 1/2011 | Fukumoto | A45D 34/04 401/66 |
| 2011/0116857 A1 * | 5/2011 | Carroll | A45D 34/04 401/101 |
| 2012/0205393 A1 | 8/2012 | Perez | |
| 2016/0174687 A1 | 6/2016 | Ellsworth | |
| 2018/0086542 A1 * | 3/2018 | Ellsworth | A45D 34/04 |
| 2018/0178968 A1 * | 6/2018 | Phipps | B65D 83/0011 |

FOREIGN PATENT DOCUMENTS

| | | |
|---|---|---|
| JP | 2011050412 A | 3/2011 |
| WO | 2010/081205 A2 | 7/2010 |

* cited by examiner

DISPENSING CONTAINER

BACKGROUND OF THE INVENTION

1. Field of Invention

The invention relates to a dispensing container for viscous products, such as cream, in particular medicinal or cosmetic cream, comprising: a cream pot having an inner cylinder that defines a storage volume configured to store a viscous product; a cap configured to close the cream pot and having a dispensing outlet; a screw rod rotatably connected to the cream pot; a piston having an inner thread and being coupled to the screw rod such that rotation of the screw rod leads to movement of the piston in the inner cylinder along a longitudinal axis of the screw rod to reduce the storage volume of the inner cylinder and to dispense the product through the dispensing outlet.

2. Description of Related Art

Such dispensing containers are known in the prior art and for example described in WO 2010/081205 A2 and EP 2 123 188 A1. The rotation of the screw rod relative to the cream pot leads to a movement of the piston relative to the cream pot because the piston is coupled to the screw rod via the internal thread to form a screw drive. Because of the axial movement of the piston, the storage volume of the inner cylinder of the cream pot is reduced, wherein pressure in the storage volume is increased. The viscous product is thereby pressed through the dispensing outlet in the cap of the dispensing container and can be wiped off from an outside surface of the cap by a user for application to the skin of the user.

Nevertheless, those prior art dispensing containers have various disadvantages. Upon dispensing action of a viscous product, the prior art dispensing containers often times vary in the dosage of the viscous product, in particular in the dosage of cream, such as medicinal cream or cosmetic cream. In particular in the area of medicinal creams, a varying dosage is undesirable. Furthermore, the prior art dispensing containers have a problem of leakage after the dispensing action. When the screw rod is rotated relative to the cream pot and the piston is thereby axially moved to reduce the storage volume and to increase the pressure in the storage volume, viscous product can leak from the dispensing outlet, even though no further dispensing action is applied to the dispensing container by the user.

Moreover, varying outside pressures which may occur during travel, for example in an airplane, may lead to leakage of viscous product from the dispensing outlet. Because of the leakage, the prior art dispensing containers are having the problem of loss of viscous product which is a big problem when expensive viscous products, such as medicinal creams, are stored in the storage volume of the dispensing container. Furthermore, the leakage of the viscous product at the dispensing outlet leads to contamination of the outside surface of the cap of the dispensing container which may also lead to contamination of the viscous product that is still stored in the storage volume.

SUMMARY OF THE INVENTION

Accordingly, it is an object of the subject invention to provide a dispensing container which avoids the above-mentioned disadvantages and drawbacks. In particular, it is an object of the subject invention to provide a dispensing container which allows a predefined dosage of the viscous product stored in the storage volume. Moreover, it is an object of the subject invention to provide a dispensing container with reduced leakage. It is furthermore an object of the subject invention to provide a dispensing container that avoids waste and provides an attractive outside appearance.

This object is solved by a dispensing container characterized in that an indexing mechanism is provided that is configured to lock the screw rod in a plurality of rotational positions with respect to the cream pot, wherein the indexing mechanism comprises indexing spring elements located at the screw rod and indexing sections located at a bottom of the cream pot, wherein the indexing spring elements of the screw rod are configured to interact with the indexing sections of the cream pot in order to lock the screw rod with respect to the cream pot. Advantageously, the indexing spring elements extend in a radial direction, i.e. perpendicular to the longitudinal axis of the screw rod, and are arranged on a collar at a bottom section of the screw rod. It is particularly preferred if the cream pot comprises a recess in which the collar and the indexing spring elements are located, wherein the indexing sections of the cream pot are located at a peripheral surface area of the recess.

Advantageously, the indexing spring elements are L-formed fingers which extend from the collar, wherein the indexing sections are sections of a circular cylinder that protrude from the peripheral surface area of the recess into the recess. The L-formed fingers may have locking sections at their free, wherein the locking sections are pre-stressed into an area between the indexing sections of the cream pot by the spring force of the indexing spring elements. It is particularly preferred if 5 indexing spring elements are provided which are uniformly distributed around the collar, wherein 10 indexing sections are provided which are also uniformly provided around the peripheral surface of the recess. By providing 10 indexing sections, an indexing resolution of 36° can be achieved. By providing the indexing mechanism, a dispensing container can be provided that allows a predefined dosage of a viscous product stored in the storage volume. Preferably, the dispensing container according to the invention is configured as a cream jar. However, it is also possible that the dispensing container has a pen-like structure and is configured as a so-called click-pen.

According to a first preferred embodiment of the dispensing container, the container comprises a lifting mechanism, in particular an intermittent lifting mechanism, that is configured to lift the screw rod from the bottom of the cream pot between a non-dispensing position and a dispensing position upon rotation of the screw rod with respect to the cream pot. In the non-dispensing position, a distance of a free end of the screw rod is advantageously bigger than a distance of the free end of the screw rod in the dispensing position. Accordingly, the piston is located closer to the dispensing outlet in the dispensing position of the screw rod. Therefore, a pressure which is built up for dispensing the viscous product can at least partly be reduced or decompressed when the screw rod and the piston are moved back into the non-dispensing position in which the piston is located further away from the dispensing outlet.

It is particularly preferred, if the lifting mechanism comprises wave-like or step-like sliding surfaces arranged at the screw rod and deflection surfaces arranged at the bottom of the cream pot, wherein rotation of the screw rod with respect to the cream pot leads to a sliding movement of the sliding surfaces on the deflection surfaces such that the screw rod is moved between the non-dispensing position and the dispensing position. By providing wave-like or step-like sliding surfaces, an intermittent up-and-down movement of the screw rod can be realized wherein the screw rod and the piston are moved upwards at the beginning of actuation action and wherein the screw rod and the piston are moved downwards at the end of actuation action.

Advantageously, the indexing mechanism is synchronized with the lifting mechanism such that the screw rod is in the non-dispensing position when rotation of the screw rod is locked with respect to the cream pot. This leads to the advantage that the pressure in the storage volume can be slightly reduced after dispensing action when the indexing mechanism locks rotational movement of the screw rod relative to the cream pot.

According to another preferred embodiment of the dispensing container, an outer decorative shell base member is provided that is configured to house the cream pot, wherein a bottom portion of the outer decorative shell base member comprises an actuating section that is configured to actuate rotational movement of the screw rod with respect to the cream pot in an actuation direction. By providing the actuating section, the screw rod and the outer decorative shell base member are rotary coupled and a rotation of the outer decorative shell base member relative to the cream pot leads to a rotation of the screw rod relative to the cream pot. Advantageously, the cream pot, the cap and the valve are configured as a self-contained and sealed unit and can be provided as an exchange part that is interchangeably housed in the outer decorative shell.

It is particularly preferred if the cream pot comprises an opening that is arranged concentrically to the cream pot and which allows actuation of the screw rod from an outside bottom portion of the cream pot. It is possible that the actuating section has a drive pattern located at a protrusion of the actuating section that corresponds with a drive pattern of a recess of the screw rod such that torque can be transmitted from the outer decorative shell member to the screw rod via the actuating section in order to actuate rotational movement of the screw rod. Advantageously, the outer decorative shell base member can be made in an attractive design with an appealing outside appearance. It is furthermore possible that an outer decorative shell cover member is provided why may be connected to the outer decorative base member, for example by mounting the outer decorative shell cover member to the outer decorative shell base member via a thread.

In order to avoid damage to the indexing mechanism, an outside bottom portion of the cream pot comprises an anti-rotation device, wherein the bottom portion of the outer decorative shell base member comprises locking features, wherein the anti-rotation device is configured to interact with the locking features so as to allow actuation of the screw rod in the actuation direction and to hinder actuation of the screw rod in a locking direction which is opposite the actuation direction. Accordingly, the screw rod which is actuated by the outer decorative shell base member can only be moved relative to the cream pot when the outer decorative shell base member is rotated relative to the cream pot in the actuation direction.

According to another preferred embodiment of the dispensing container, an outside bottom portion of the cream pot comprises a mounting ring having an annular undercut, wherein the outer decorative shell base member comprises mounting features having undercuts, wherein the undercut of the mounting ring interact with the undercuts of the mounting features to fasten the cream pot in the outer decorative shell base member. It is also possible that the outside bottom portion of the cream pot comprises the mounting features wherein the mounting ring is provided on the outer decorative shell base member, wherein the undercut of the mounting ring interacts with the undercuts of the mounting features as mentioned above-Advantageously, the outer decorative shell base member comprises a base part made from glass or metal and a function part made from plastic connected to the base part, wherein the function part comprises the actuating section, the locking features and the mounting features. Therefore it is possible to manufacture the actuating section, the locking features and the mounting features in an easy and cost-efficient manner from a plastic, for example by injection molding, wherein an attractive design with an appealing outside appearance can be achieved by use of higher quality materials such as glass or metal. However, it is also possible that the base part is made from plastic or other materials.

In order to avoid leakage of the viscous product from the dispensing outlet, a valve is provided that is configured to close the dispensing outlet.

It is particularly preferred if the valve comprises a valve member, wherein a valve opening mechanism is provided that is configured to move the valve member along the longitudinal axis of the screw rod between a closed position in which the dispensing outlet is closed by the valve member and an open position in which the dispensing outlet is open, wherein the screw rod comprises valve actuating features, that are configured to rotate the valve member about the longitudinal axis of the screw rod with respect to the cap, thereby actuating the valve opening mechanism. Accordingly it is possible to open the valve for dispensing the viscous product wherein the valve member closes the dispensing outlet after dispensing action, thereby preventing leakage from the dispensing outlet.

According to another preferred embodiment of the dispensing container, the valve opening mechanism comprises valve opening features arranged at the cap and wave-like or step-like valve lifting features arranged at the valve member, wherein the valve opening features and the valve lifting features are configured to move the valve member between the closed position and the open position upon rotation of the valve member about the longitudinal axis of the screw rod with respect to the cap. Preferably, the wave-like or step-like valve lifting features slide upon the valve opening features of the cap, wherein the rotational movement leads to an axial displacement of the valve member along the longitudinal axis of the screw rod. Accordingly, the valve can be opened and closed by rotating the screw rod relative to the cream pot and the cap, thereby moving the valve member between the closed and the open position and back.

Preferably, a spring member is provided that is connected to the cap and configured to preload the valve member into the closed position. Advantageously, the spring member comprises an annular mounting ring that is connected to the cap. For connection of the spring member to the cap, the cap comprises a ring-shaped protrusion with an undercut wherein the mounting ring is connected to the protrusion in a form fitting manner. Preferably, the spring member comprises a plurality of spring arms, in particular 3 spring arms that are configured to pre-stress the valve member into the closed position.

Advantageously, the cream pot comprises a plurality of guiding sections, which are arranged on an outer circumference of the cream pot, wherein the cap comprises a plurality of guiding bridges, wherein the guiding sections are configured to guide the guiding bridges into a predetermined position when the cap is mounted to the cream pot.

Preferably, the guiding sections are triangularly shaped and spaced apart in a distance which is slightly bigger than a width of the guiding bridges. Accordingly it is possible that the guiding bridges slide into the spaces between the guiding sections in order to mount the cap to the cream pot in a predetermined position. Preferably, the guiding bridges are aligned with the valve opening features of the cap such that the valve opening features can be placed at a predetermined position when the cap is mounted to the cream pot. Accordingly, the up and down movement of the valve member can be adjusted by mounting the cap at a predetermined position.

Furthermore, it is particularly preferred if the lifting mechanism and the valve opening mechanism are synchronized such that the valve is in the closed position when the screw rod is in the non-dispensing position and that the valve is in the open position when the screw rod is in the dispensing position. Thereby, leakage of the viscous product from the dispensing outlet can be reliably avoided because the valve is only in the open position when the screw rod in the dispensing position.

According to another preferred embodiment of the dispensing container, a cover area of the cap is curved axially inwardly towards the inner cylinder of the cream pot, wherein an inner surface of the cap at the cover area corresponds with an upper surface of the piston. Preferably, the cover area is curved axially inwardly towards the dispensing outlet. By providing a cover area of the cap with such a curvature, the upper surface of the piston almost fully abuts the inner surface of the cap at the cover area when the piston is at its upper dead point. Accordingly, the storage volume of the dispensing container can be almost fully emptied. By curving the cover area towards the dispensing outlet, viscous product will be preferably guided towards the dispensing outlet when the piston is moved upwards towards the cap.

Advantageously, a gasket is provided that is arranged between the screw rod and the cream pot, wherein the gasket is configured to prevent leakage between the screw rod and the cream pot. Providing such a gasket is particularly preferable because air contact of the viscous product which may lead to decomposition of the viscous product can be minimized. Preferably, the gasket is ring-shaped. It is particularly preferred if the gasket is permeable to air when the screw rod is moved into the dispensing position. This may be achieved by providing a gasket contact section at the screw rod which abuts the gasket when the screw rod is in the non-dispensing position and which is lifted from the gasket when the screw rod is moved into the dispensing position. Accordingly, air can flow into the storage volume upon actuation of the screw rod to compensate for the dispensed viscous product in order to prevent vacuum generation in the storage volume.

Furthermore, it is particularly preferred if the screw rod comprises a shaft having an unthreaded section, wherein the piston has an inner unthreaded section, wherein an outer diameter of the unthreaded section of the shaft is bigger than an inner diameter of the inner unthreaded section, such that a bearing seal is formed between the unthreaded section of the shaft and the inner unthreaded section of the piston. Preferably, the unthreaded section of the shaft is arranged at a lower portion of the screw rod between the threaded section of the shaft and the indexing spring elements. Leakage of viscous product at the thread between piston and screw rod is possible. Accordingly, a pre-sealing can be provided when the dispensing container is unused in the delivery state, thereby preventing leakage of the viscous product at the thread between piston and screw rod when the dispensing container is offered for sale in a pharmacy or drug store.

According to another preferred embodiment of the dispensing container, the cream pot comprises an annular sealing wall that is arranged concentrically to and radially outside of the inner cylinder, wherein the cap comprises an annular sealing lip at an interior area of the cap, which is configured to sealingly abut against the sealing wall when the cap is mounted to the cream pot. On the one hand, a reliable sealing can be provided between the cap and the cream pot. On the other hand, the piston can be moved to its upper dead point in the inner cylinder wherein restriction of the movement by the sealing lips of the cap can be avoided.

Further details and advantages of the invention can be taken from the following description, on the basis of which the embodiment of the invention that is represented in the figures is described and explained in more detail.

BRIEF DESCRIPTION OF THE DRAWING

The Drawing includes FIGS. 1-20, as follows.

DETAILED DESCRIPTION OF THE BEST MODE OF THE INVENTION

Figure 1:
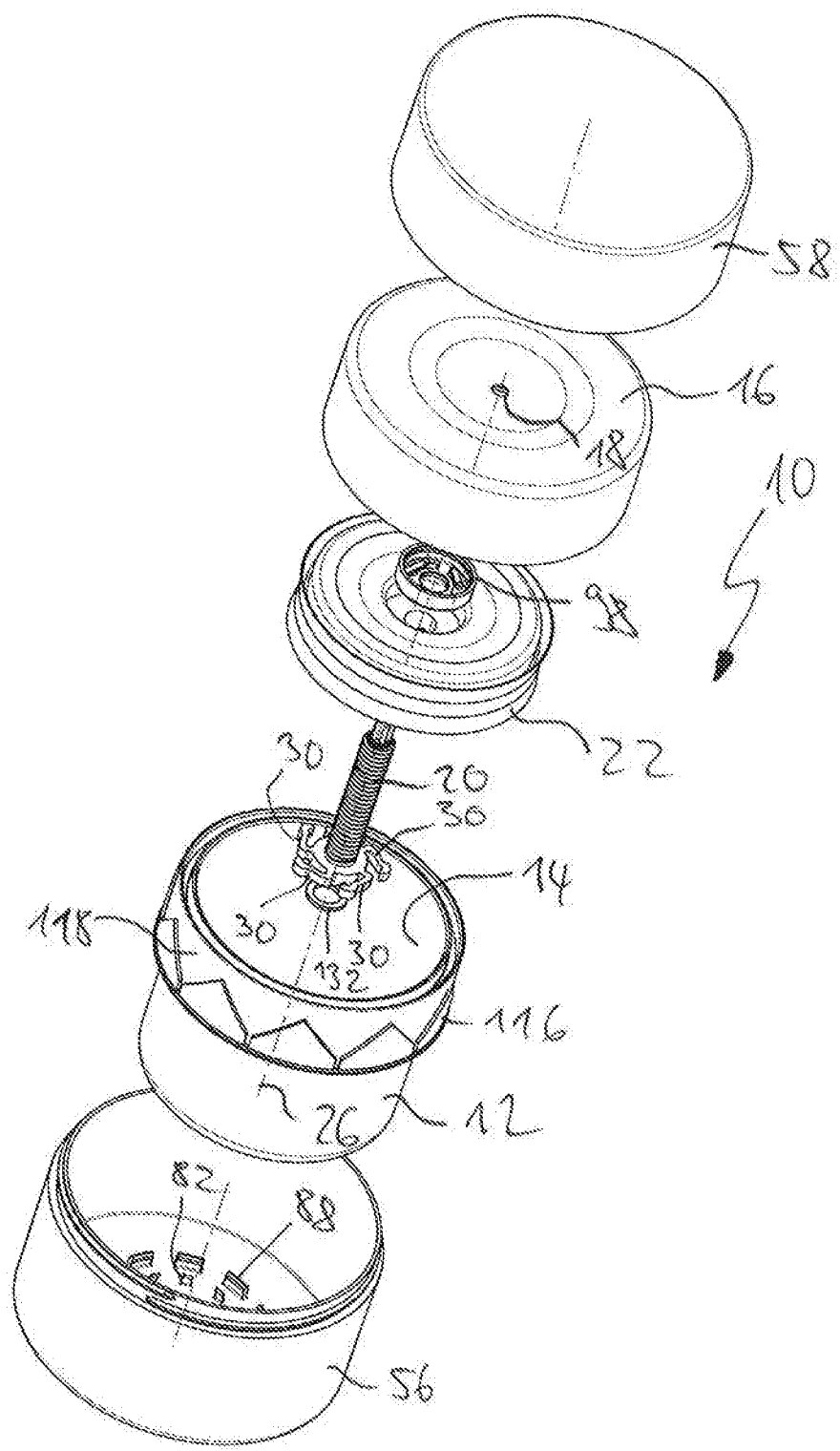
FIG. 1 an exploded top perspective view of the dispensing container according to the invention.

In FIGS. 1 to 20 a dispensing container 10 is shown. FIG. 1 shows an exploded top perspective view of the dispensing container 10. The dispensing container 10 is configured to dispense viscous products, such as cream, in particular medicinal or cosmetic cream.

As shown in FIG. 1, the dispensing container 10 comprises a cream pot 12 having an inner cylinder 14 that defines a storage volume configured to store the viscous product. The dispensing container 10 comprises a cap 16 that is configured to close the cream pot 12 and that has a dispensing outlet 18. The cap 16 and the cream pot 12 are made of Polypropylene (PP). Furthermore, the dispensing container 10 comprises a screw rod 20 and a piston 22. The screw rod 20 is rotatably connected to the cream pot 12. The screw rod 20 is made of Polypropylene (PP) or Polyoxymethylene (POM) and the piston 22 is made of Polyethylene (PE). As shown for example in FIGS. 2 and 3, the piston 22 has an inner thread 24 and is coupled to the screw rod 20 such that rotation of the screw rod 20 leads to movement of the piston 22 in the inner cylinder 14 along a longitudinal axis 26 of the screw rod 20 to reduce the storage volume of the inner cylinder 14 and to dispense the product through the dispensing outlet 18.

As shown in particular in FIGS. 2 to 4 and 6 to 8, the dispensing container 10 comprises an indexing mechanism 28 that is configured to lock the screw rod 20 in a plurality of rotational positions with respect to the cream pot 12. This indexing mechanism 28 comprises indexing spring elements 30 located at the screw rod 20 and indexing sections 32 located at a bottom of the cream pot 12.

The indexing spring elements 30 extend in a radial direction, i.e. perpendicular to the longitudinal axis 26 of the screw rod and are arranged on a collar 34 at a bottom section 36 of the screw rod 20. The indexing spring elements 30 are L-formed fingers which extend from the collar 34 and which have locking sections 38 at their free end 40.

The indexing sections 32 are sections of a circular cylinder that protrude from a peripheral surface 42 area of a recess 44 in the cream pot 12 into the recess 44. The collar 34 and the indexing spring elements 30 are located in the recess 44.

The locking sections 38 of the indexing spring elements 30 are pre-stressed into an area between the indexing sections 32 of the cream pot 12 by the spring force of the indexing spring elements 30. Accordingly, the indexing spring elements 30 of the screw rod 20 are configured to interact with the indexing sections 32 of the cream pot 12 in order to lock the screw rod 20 with respect to the cream pot 12.

Figure 5:
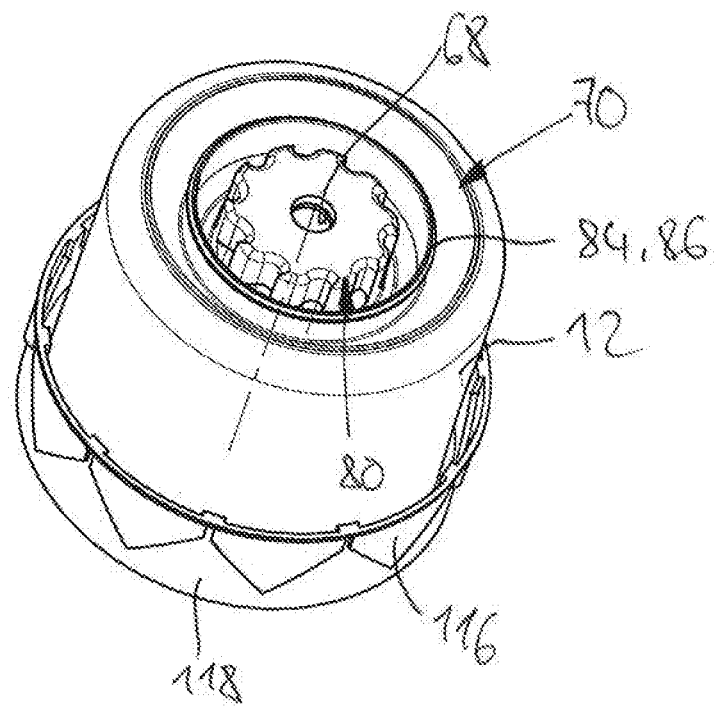
FIG. 5 a bottom perspective view of a cream pot of the dispensing container of FIG. 1.
Figure 7:
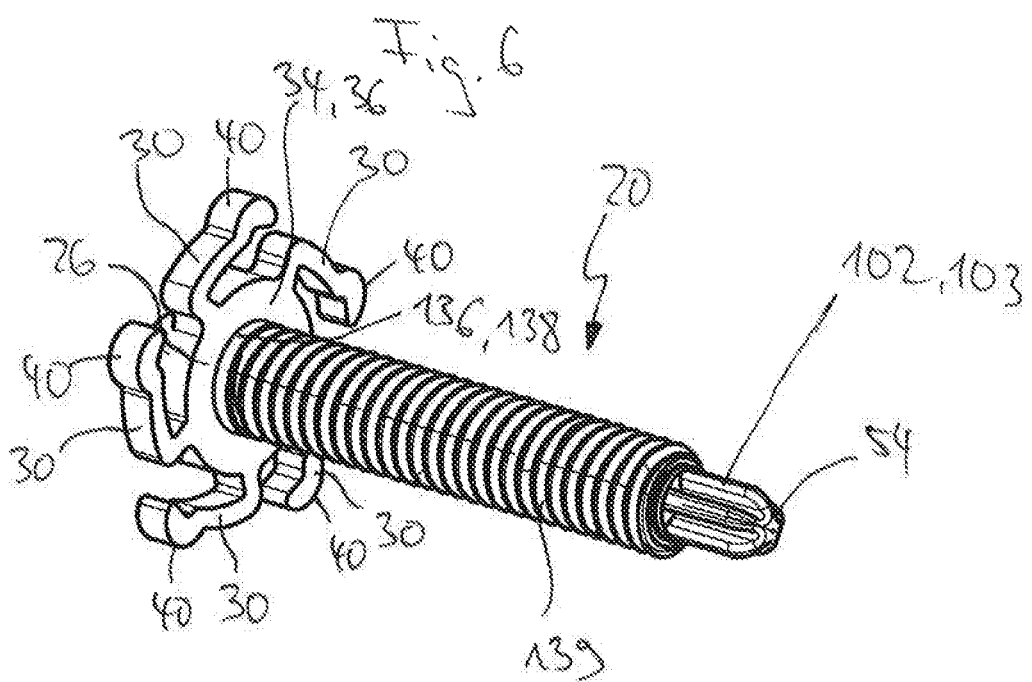
FIG. 7 a front perspective view of a screw rod of the dispensing container of FIG. 1.
Figure 8:
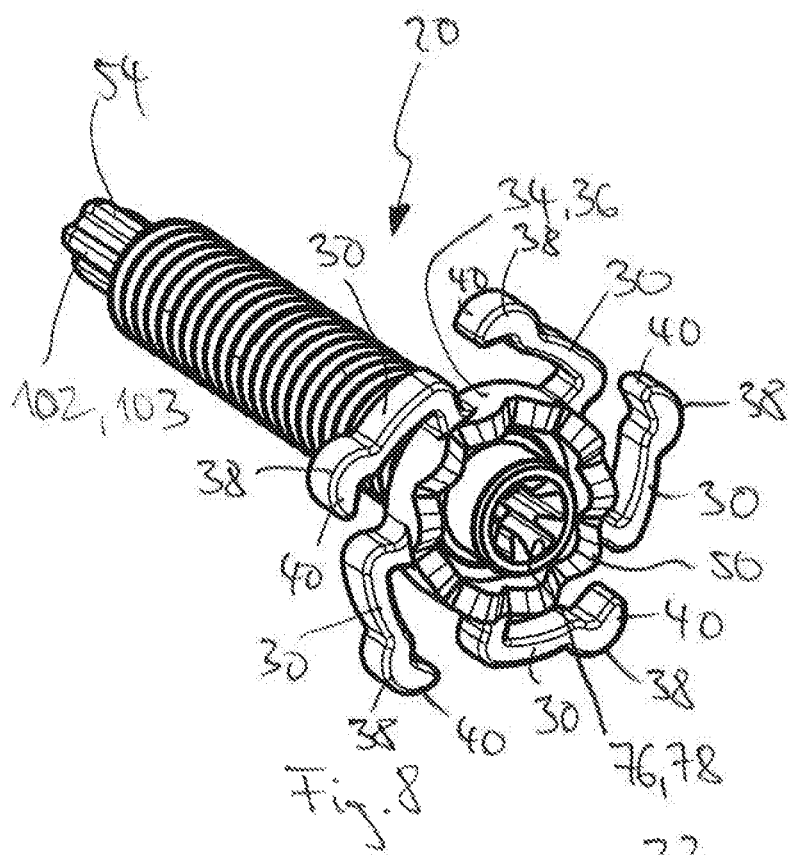
FIG. 8 a rear perspective view of the screw rod of FIG. 7.

As shown in FIGS. 7 and 8, 5 indexing spring elements 30 are provided which are uniformly distributed around the collar 34. Moreover, 10 indexing sections 32 are provided which are also uniformly provided around the peripheral surface 42 of the recess 44. By providing 10 indexing sections, an indexing resolution of 36° can be achieved. By use of the indexing mechanism 28, a dispensing container 10 can be provided that allows a predefined dosage of a viscous product stored in the storage volume of the inner cylinder 14.

Figure 4:
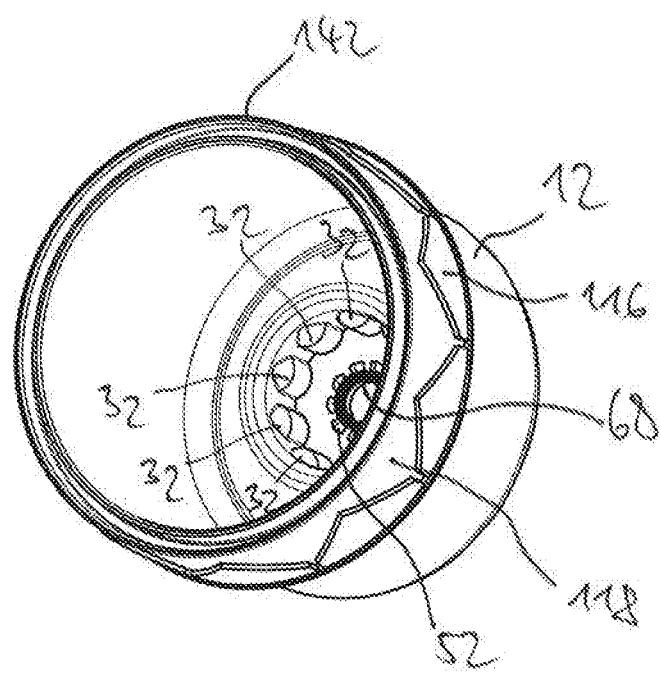
FIG. 4 a top perspective view of a cream pot of the dispensing container of FIG. 1.
Figure 6:
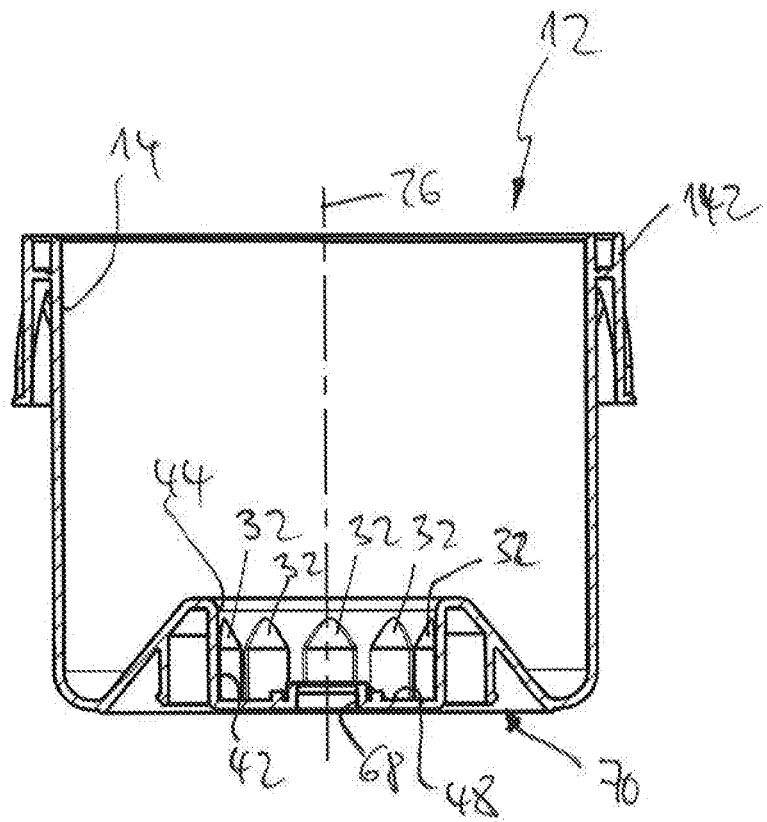
FIG. 6 a sectional view of the cream pot of FIGS. 4 and 5.

As shown in a combination of FIGS. 4, 6 and 8, the dispensing container 10 comprises a lifting mechanism 46 that is configured to lift the screw rod 20 from a bottom 48 of the cream pot 12 between a non-dispensing position and a dispensing position upon rotation of the screw rod 20 with respect to the cream pot 12. The lifting mechanism 46 comprises wave-like or step-like sliding surfaces 50 (FIG. 8) arranged at the screw rod 20 and deflection surfaces 52 arranged at the bottom 48 of the cream pot 12 (see FIGS. 4 and 6). Rotation of the screw rod 20 with respect to the cream pot 12 leads to a sliding movement of the sliding surfaces 50 on the deflection surfaces 52 such that the screw rod 20 is moved between the non-dispensing position and the dispensing position. In the non-dispensing position, a distance of a free end 54 of the screw rod 20 to the cap 16 is bigger than a distance of the free end 54 of the screw rod 20 to the cap 16 in the dispensing position. Accordingly, the piston 22 is located closer to the dispensing outlet 18 in the dispensing position of the screw rod 20.

By providing the wave-like or step-like sliding surfaces 50, an up-and-down movement of the screw rod 20 can be realized wherein the screw rod 20 and the piston 22 are moved upwards at the beginning of actuation action and wherein the screw rod 20 and the piston 22 are moved downwards at the end of actuation action. Therefore, a pressure which is built up for dispensing the viscous product can at least partly be reduced when the screw rod 20 and the piston 22 are moved back into the non-dispensing position in which the piston 22 is located further away from the dispensing outlet 18.

As shown in FIGS. 4 and 6 to 8, the indexing spring elements 30 of the screw rod 20 and the wave-like or step-like sliding surfaces 50 are arranged in a predetermined position with respect to each other. Moreover, the deflection surfaces 52 and the indexing sections 30 of the cream pot 12 are arranged in a predetermined position with respect to each other. 10 wave-like or step-like sliding surfaces 50 and also 10 deflection surfaces 52 are provided, such that the indexing mechanism 28 is synchronized with the lifting mechanism 46 such that the screw rod 20 is in the non-dispensing position when rotation of the screw rod 20 is locked with respect to the cream pot 12. This leads to the advantage that the pressure in the storage volume of the inner cylinder 14 can be slightly reduced after dispensing action when the indexing mechanism 28 locks rotational movement of the screw rod 20 relative to the cream pot 12.

Figure 2:
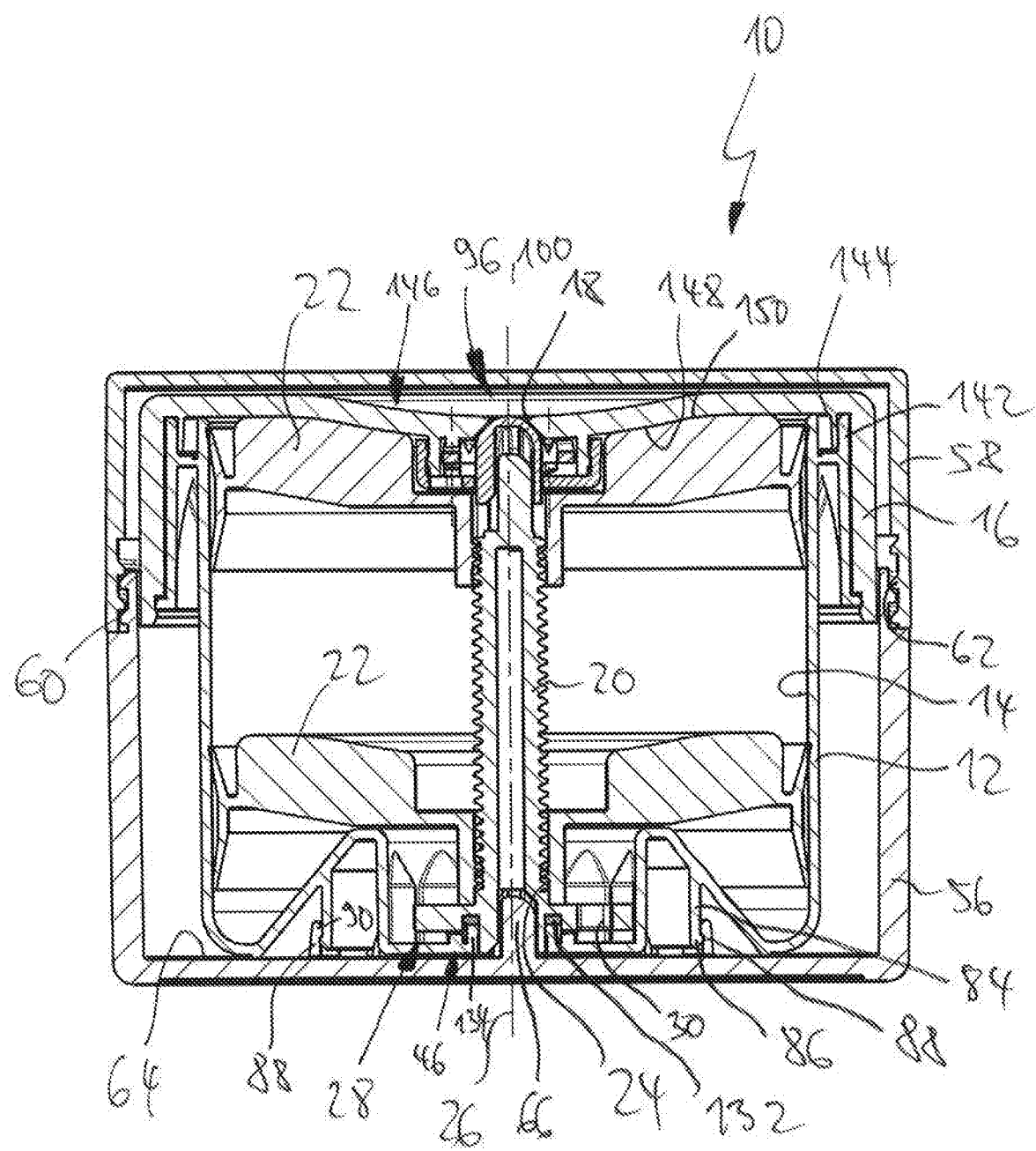
FIG. 2 a sectional view of the dispensing container of FIG. 1.

Coming back to FIGS. 1 and 2, the dispensing container 10 comprises an outer decorative shell base member 56 that is provided that is configured to house the cream pot 12. The dispensing container 10 furthermore comprises an outer decorative shell cover member 58 which may be connected to the outer decorative base member 56 by mounting the outer decorative shell cover member 58 to the outer decorative shell base member 58 via an external thread 60 of the outer decorative shell base member 56 and via an internal thread 62 of the outer decorative shell cover member 58.

A bottom portion 64 of the outer decorative shell base member 56 comprises an actuating section 66 that is configured to actuate rotational movement of the screw rod 20 with respect to the cream pot 12 in an actuation direction. The cream pot 12 has an opening 68 that is arranged concentrically to the cream pot 12 and that allows actuation of the screw rod 20 from an outside bottom portion 70 of the cream pot 12.

In order to actuate rotational movement of the screw rod 20 with respect to the cream pot 12, the actuating section 66 has a drive pattern 72 located at a protrusion 74 of the actuating section 66 that corresponds with a drive pattern 76 of a recess 78 of the screw rod 20 (see FIG. 8) such that torque can be transmitted from the outer decorative shell member 56 to the screw rod 20 via the actuating section 66 in order to actuate rotational movement of the screw rod 20. The protrusion 74 is located in the opening 68 of the cream pot 12.

By providing the actuating section 66, the screw rod 20 and the outer decorative shell base member 56 are rotary coupled and a rotation of the outer decorative shell base member 56 relative to the cream pot 12 leads to a rotation of the screw rod 20 relative to the cream pot 12.

In order to avoid an operating error, the outside bottom portion 70 of the cream pot 12 comprises an anti-rotation device 80 with a saw tooth profile. The bottom portion 64 of the outer decorative shell base member 64 comprises locking features 82. The anti-rotation device 80 is configured to interact with the locking features 82 so as to allow actuation of the screw rod 20 in the actuation direction and to hinder actuation of the screw rod 20 in a locking direction which is opposite the actuation direction. The anti-rotation device 80 comprises 10 saw teeth which are arranged such as to synchronize the anti-rotation device 80 with the indexing mechanism 28 and with the indexing mechanism 46.

The outer decorative shell base member 56 can only be moved relative to the cream pot 12 when the outer decorative shell base member 56 is rotated relative to the cream pot 12 in the actuation direction. Accordingly, the screw rod 20 can only be moved relative to the cream pot 12 when the outer decorative shell base member 56 is rotated relative to the cream pot 12 in the actuation direction.

In order to mount the cream pot 12 to the outer decorative shell base member 56, the outside bottom portion 70 of the cream pot 12 comprises a mounting ring 84 having an annular undercut 86. The outer decorative shell base member 56 comprises mounting features 88 having undercuts 90. The undercut 86 of the mounting ring 84 interacts with the undercuts 90 of the mounting features 88 to fasten the cream pot 12 in the outer decorative shell base member 56.

The outer decorative shell base member 56 may have an attractive design with an appealing outside appearance, This can be achieved by use of higher quality materials such as glass or metal. Accordingly, the outer decorative shell base member 56 may comprise a base part 92 made from glass or metal and a function part 94 made from plastic connected to the base part 92, wherein the function part 94 comprises the actuating section 66, the locking features 82 and the mounting features 88. Accordingly it is possible to manufacture the actuating section 66, the locking features 82 and the mounting features 88 in an easy and cost-efficient manner from a plastic, for example by injection molding.

Figure 3:
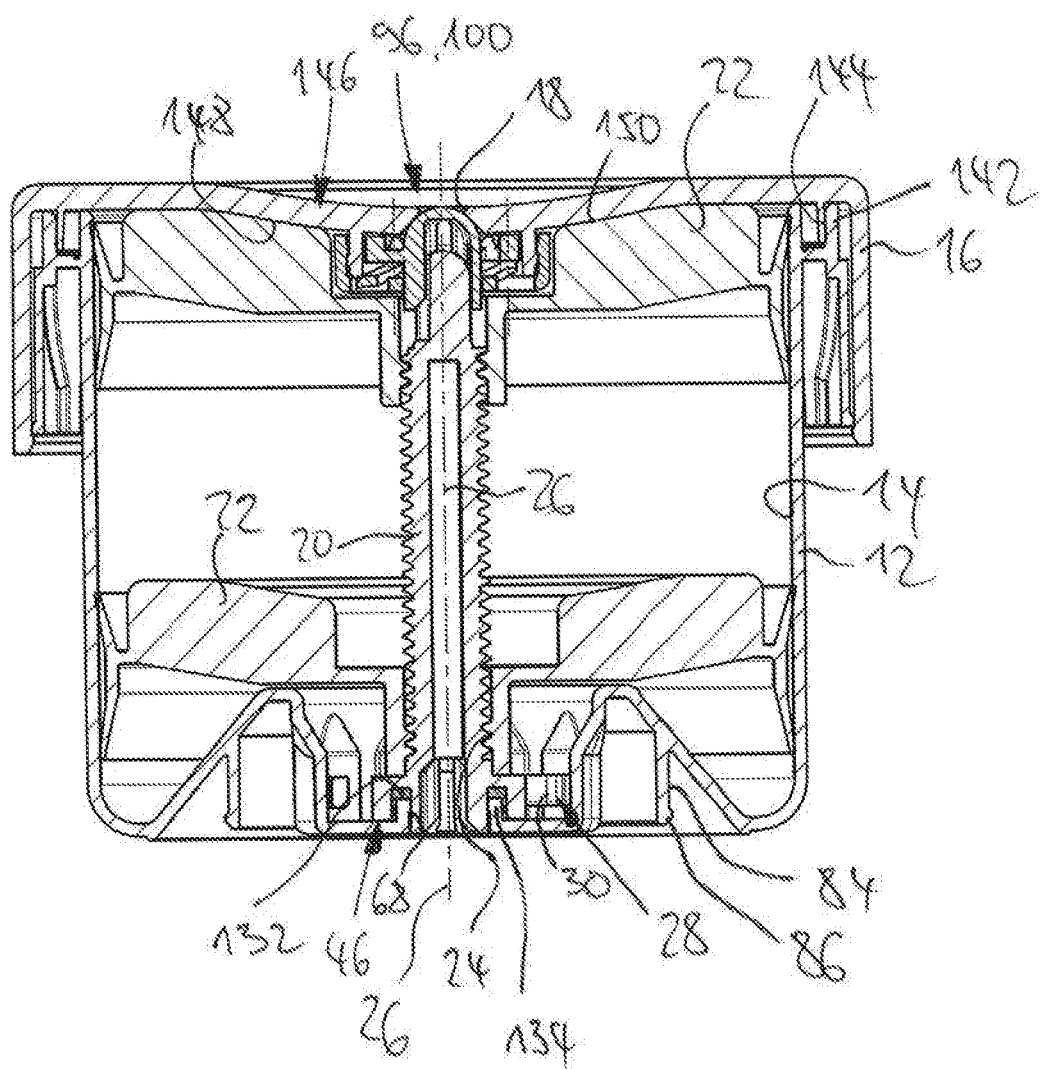
FIG. 3 the sectional view of the dispensing container of FIG. 2 without outer decorative shell.

Coming back to FIGS. 2 and 3, a valve 96 is provided that is configured to close the dispensing outlet 18 in order to avoid leakage of the viscous product from the dispensing outlet 18.

Figure 12:
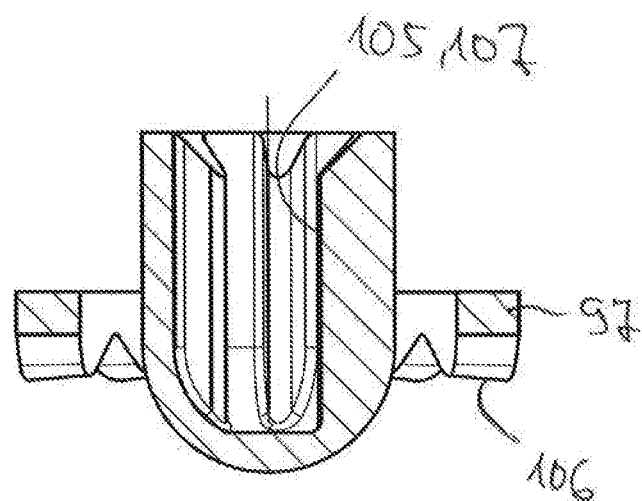
FIG. 12 a sectional view of a valve member of the dispensing container of FIG. 1.
Figure 13:
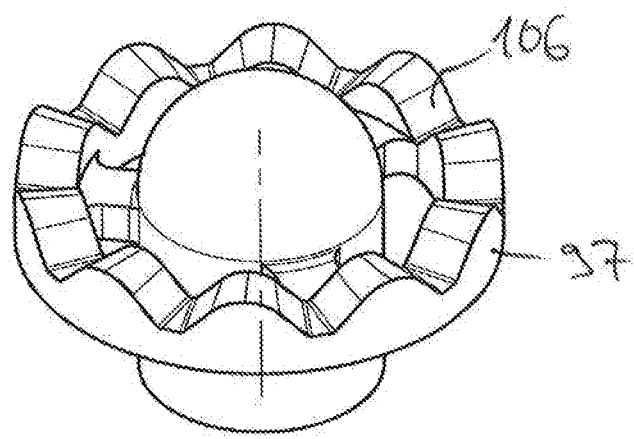
FIG. 13 a bottom perspective view of the valve member of FIG. 12.
Figure 14:
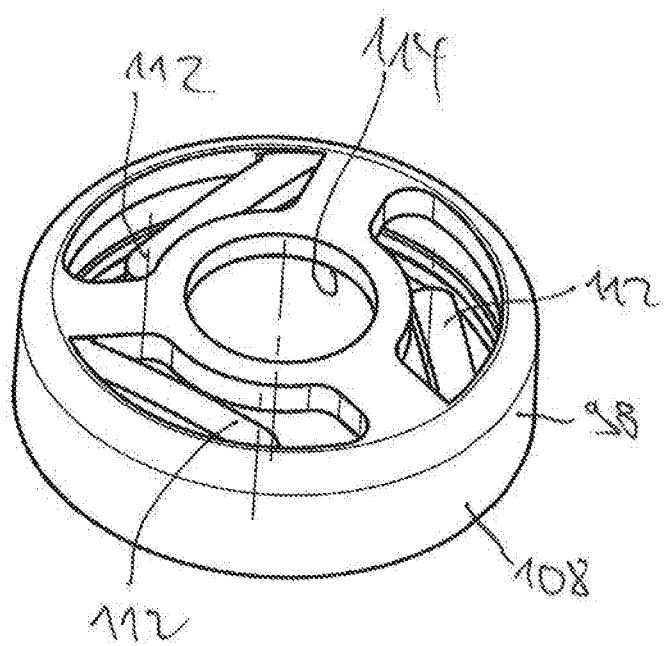
FIG. 14 a top perspective view of a spring member of the dispensing container of FIG. 1.
Figure 15:
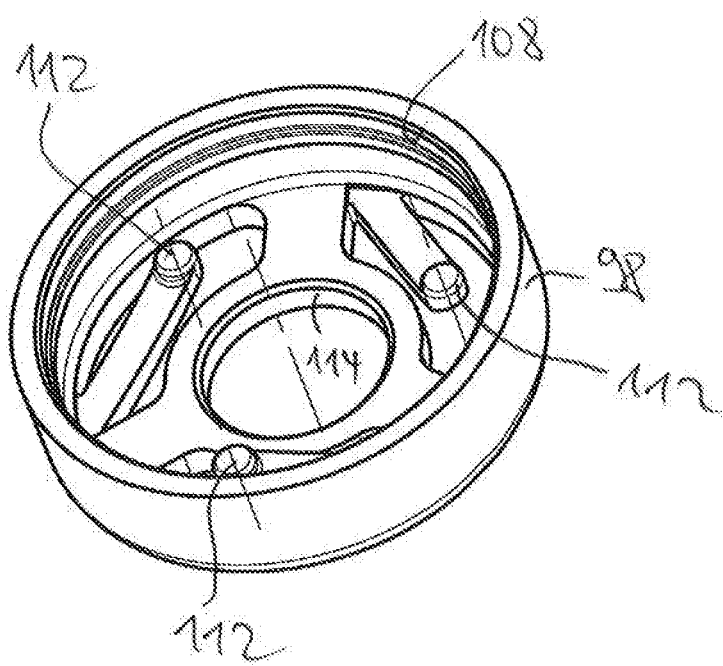
FIG. 15 a bottom perspective view of the spring member of FIG. 14.
Figure 16:
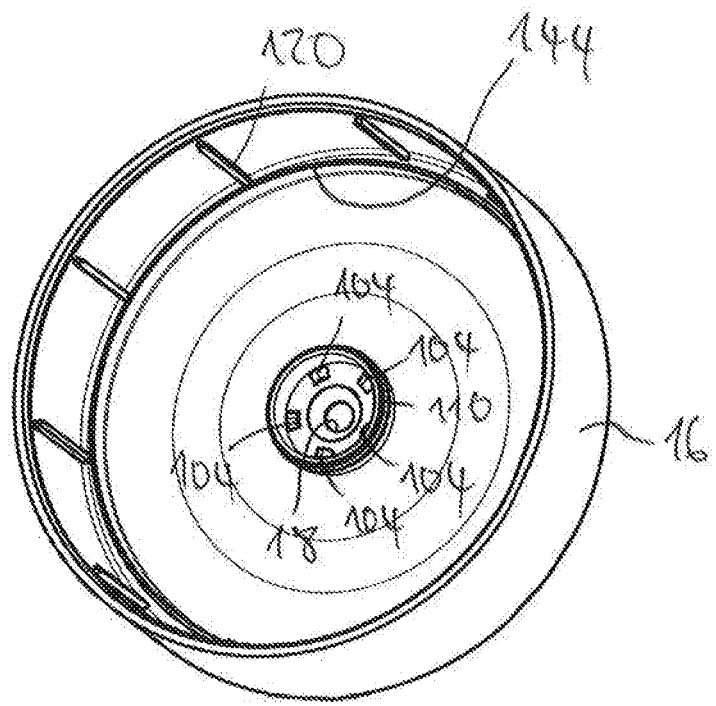
FIG. 16 a bottom perspective view of a cap of the dispensing container of FIG. 1.
Figure 17:
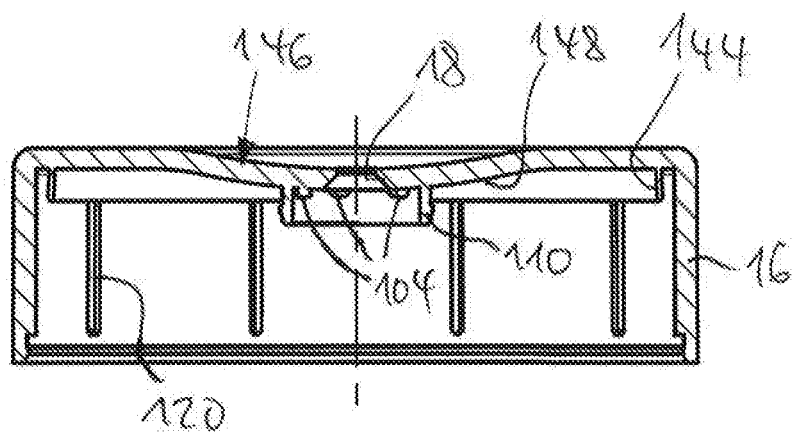
FIG. 17 a sectional view of the cap of FIG. 16.
Figure 18:
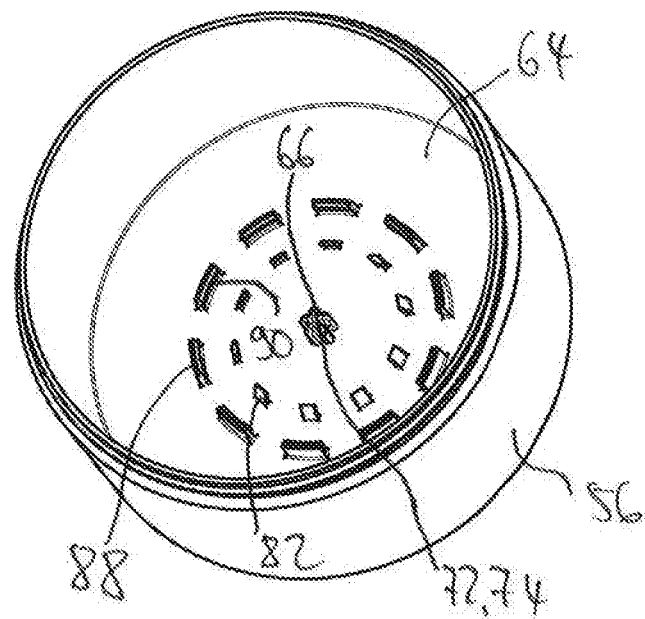
FIG. 18 a top perspective view of an outer decorative shell base member of the dispensing container of FIG. 1.
Figure 19:
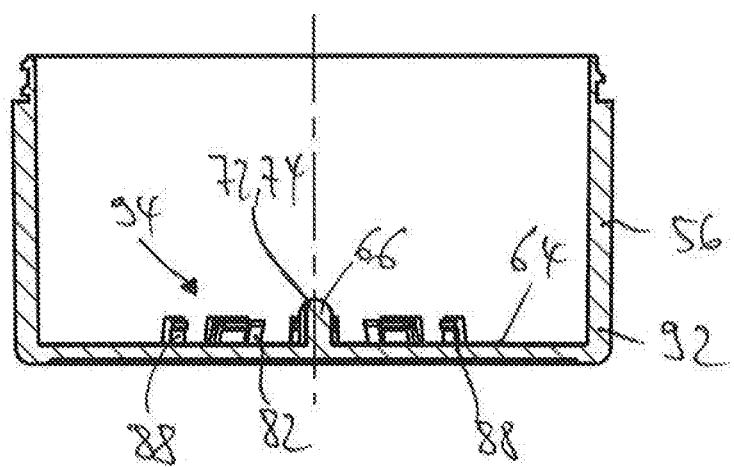
FIG. 19 a sectional view of the outer decorative shell base member of FIG. 18.
Figure 20:
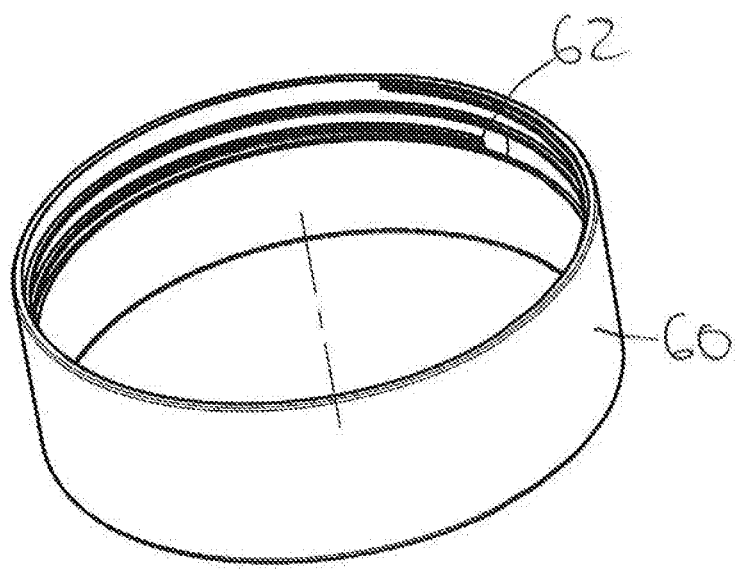
FIG. 20 a bottom perspective view of an outer decorative shell cover member of the dispensing container.

The valve 96 comprises a valve member 97 with a hemi-spherical head that is shown in FIGS. 12 and 13 and a spring member 98 that is shown in FIGS. 14 and 15. In order to open and close the valve 96, a valve opening mechanism 100 is provided that is configured to move the valve member 97 along the longitudinal axis 26 of the screw rod 20 between a closed position in which the dispensing outlet 18 is closed by the valve member 97 and an open position in which the dispensing outlet 18 is open.

In order to actuate the valve opening mechanism 100, the screw rod 20 comprises valve actuating features 102 arranged at the free end 54 of the screw rod, that are configured to rotate the valve member 97 about the longitudinal axis 26 of the screw rod 20 with respect to the cap 16, thereby actuating the valve opening mechanism 10. The valve actuating features 102 are having a drive pattern 103 that correspond with a drive pattern 105 of a recess 107 in the valve member 97.

The valve opening mechanism 100 comprises valve opening features 104 arranged at the cap 16 (see FIGS. 16 and 17) and wave-like or step-like valve lifting features 106 arranged at the valve member 97. The valve opening features 104 and the valve lifting features 106 are configured to move the valve member 97 between the closed position and the open position upon rotation of the valve member 97 about the longitudinal axis 26 of the screw rod 20 with respect to the cap 16

The wave-like or step-like valve lifting features 106 slide upon the valve opening features 104 of the cap 20, wherein the rotational movement leads to an axial displacement of the valve member 97 along the longitudinal axis 26 of the screw rod 20. Accordingly, the valve 96 can be opened and closed by rotating the screw rod 20 relative to the cream pot 12 and the cap 16, thereby moving the valve member 97 between the closed and the open position and back.

The spring member 98 is configured to preload the valve member 97 into the closed position. The spring member 98 comprises an annular mounting ring 108 that is connected to the cap 16. For connection of the spring member 98 to the cap 16, the cap 16 comprises a ring-shaped protrusion 110 with an undercut wherein the mounting ring 108 is connected to the protrusion 110 in a form fitting manner. The spring member 98 comprises spring arms 112 that are configured to pre-stress the valve member 97 into the closed position. The spring arms 112 are arranged around an opening 114 of the spring member 98 through which the valve member 97 is guided.

The lifting mechanism 46 and the valve opening mechanism 100 are synchronized such that the valve 96 is in the closed position when the screw rod 20 is in the non-dispensing position and such that the valve 96 is in the open position when the screw rod 20 is in the dispensing position. Thereby, leakage of the viscous product from the dispensing outlet 18 can be reliably avoided because the valve 96 is only in the open position when the screw rod 20 is in the dispensing position.

In order to assure synchronization of the lifting mechanism 46 and the valve opening mechanism 100, the cap 16 has be to mounted to the cream pot 12 in a predefined position.

Accordingly, the cream pot 12 comprises a plurality of guiding sections 116, which are arranged on an outer circumference 118 of the cream pot 12 (see FIGS. 1, 4 and 5). The cap 16 comprises a plurality of guiding bridges 120 that are arranged parallel to the longitudinal axis 26 (see FIGS. 16 and 17). The guiding sections 116 are configured to guide the guiding bridges 120 into the predetermined position when the cap 16 is mounted to the cream pot 12. Therefore, the guiding sections 116 are triangularly shaped and spaced apart in a distance which is slightly bigger than a width of the guiding bridges 120. Accordingly it is possible that the guiding bridges 120 slide into the spaces between the guiding sections 116 in order to mount the cap 16 to the cream pot 12 in the predetermined position In order to synchronize the lifting mechanism 46 and the valve opening mechanism 100, the guiding bridges 120 are aligned with the valve opening features 104 of the cap 16 such that the valve opening features 104 can be placed at the predetermined position when the cap 16 is mounted to the cream pot 12. Accordingly, the synchronized up and down movement of the valve member 96 can be adjusted by mounting the cap 16 at the predetermined position.

The dispensing container 10 comprises further sealing features in order to prevent leakage of the viscous product from the dispensing container and in order to avoid aging of the viscous product due to contact with air and/or oxygen.

Figure 9:
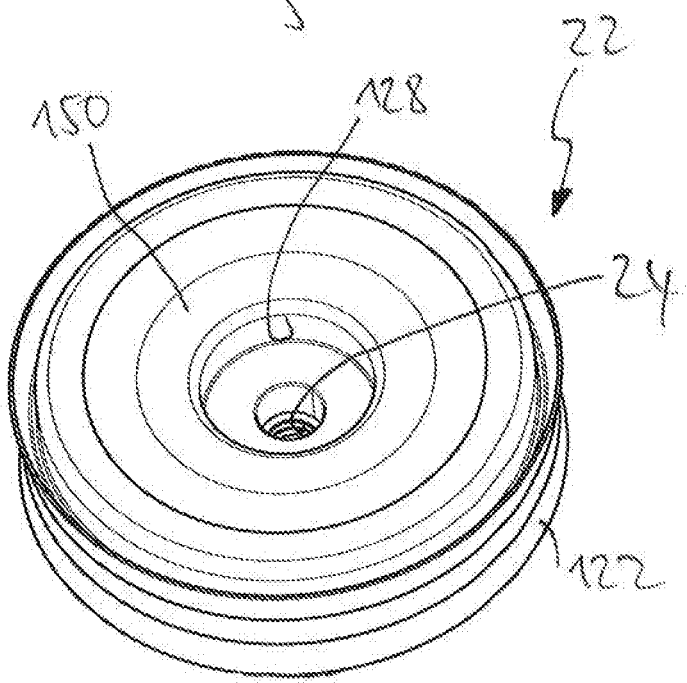
FIG. 9 a top perspective view of a piston of the dispensing container of FIG. 1.
Figure 10:
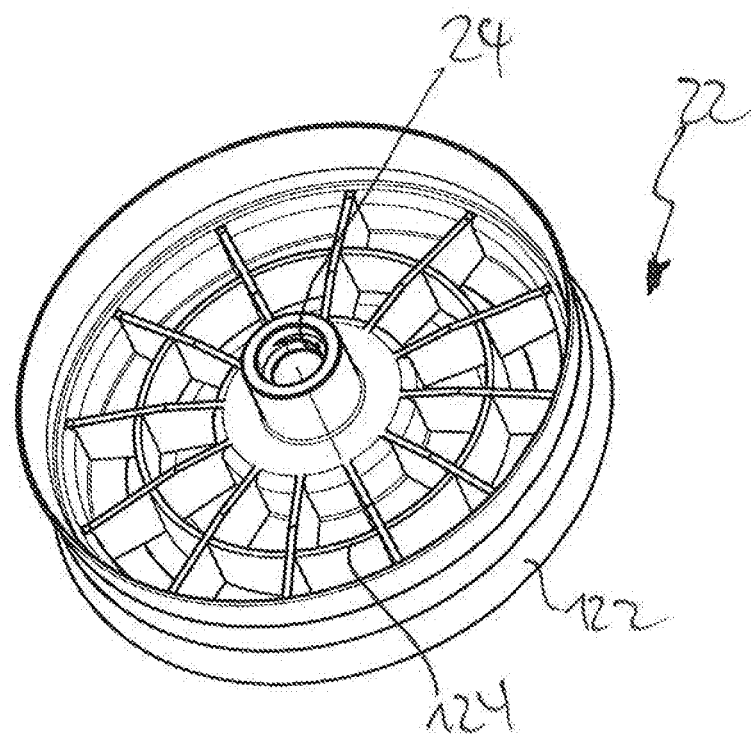
FIG. 10 a bottom perspective view of the piston of FIG. 9.
Figure 11:
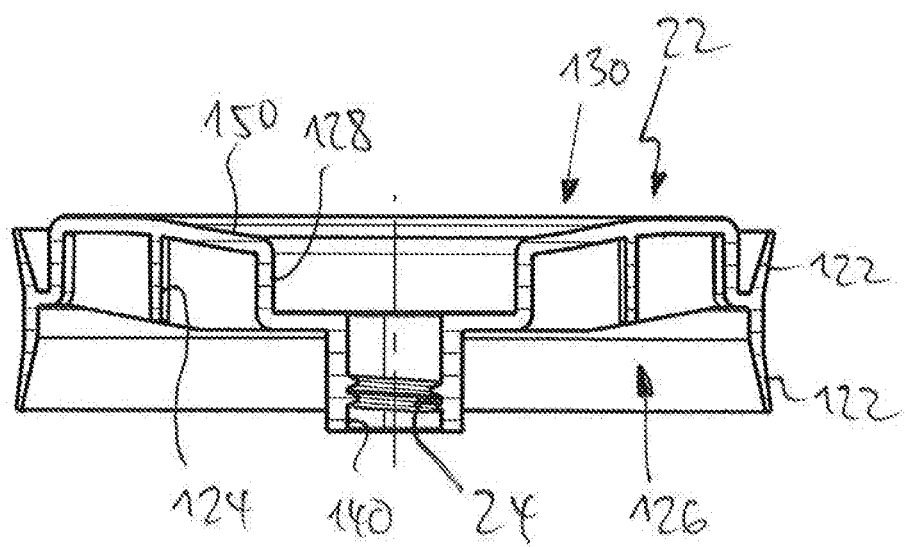
FIG. 11 a sectional view of the piston of FIGS. 9 and 10.

The piston 22 that is shown in FIGS. 9 to 11 has sealing lips 122 that abut the inner cylinder 14 of the cream pot 12 in order to avoid that viscous product leaks between the inner cylinder 14 and the piston 22 when the storage volume is reduced and the pressure is raised by moving up the piston 22 towards the dispensing outlet 18. The piston 22 that is made of Polyethylene (PE) comprises a plurality of stiffening ribs 124 on its bottom side 126 and a central recess 128 that is arranged on the top side 130 of the piston 22 and configured to house the valve 96 when the piston 22 is at its upper dead point.

FIGS. 2 and 3 show the piston 22 in the two extreme positions, namely in the lower dead point and in the upper dead point, respectively.

Since the Polyethylene (PE) material of the piston 22 is permeable to air and/or oxygen, a ring-shaped gasket 132 is provided (see FIG. 1) that is arranged between the screw rod 20 and the cream pot 12.

A gasket contact section 134 is provided at the cream pot 12 and/or at the screw rod 20 which abuts the gasket 132 when the screw rod 20 is in the non-dispensing position and which is lifted from the gasket 132 when the screw rod 20 is moved into the dispensing position. Accordingly, the gasket 132 is permeable to air when the screw rod 20 is moved into the dispensing position, wherein the gasket 132 is configured to prevent leakage between the screw rod 20 and the cream pot when the screw rod 20 is in the non-dispensing position. Air can only flow into the storage volume upon actuation of the screw rod 20 to compensate for the dispensed viscous product in order to prevent vacuum generation in the storage volume.

By providing gasket 132, decomposition of the viscous product because of air and/or oxygen contact can be minimized.

In order to avoid leakage of the viscous product between the piston 22 and the screw rod 20 at the inner thread 24 of the piston, in particular when the dispensing container 10 is unused in the delivery state and offered for sale in a pharmacy or drug store, the screw rod 20 comprises a shaft 136 having an unthreaded section 138 (see FIG. 7) arranged at a lower portion of the screw rod 22 between the threaded section 139 of the shaft 136 and the indexing spring elements 30. The piston 22 has an inner unthreaded section 140 (see FIG. 11). An outer diameter of the unthreaded section 138 of the shaft 136 is bigger than an inner diameter of the inner unthreaded section 140 of the piston 22 such that a bearing seal is formed between the unthreaded section 138 of the shaft 136 and the inner unthreaded section 140 of the piston 22.

By providing the bearing sealing between the unthreaded sections 138, 140 pre-sealing can be provided when the dispensing container 10 is unused in the delivery state, thereby preventing leakage of the viscous product.

In order to seal the cap 16 to the cream pot 12 so as to avoid leakage of the viscous product at an interface area of the cream pot 12 and the cap 16, the cream pot 12 comprises an annular sealing wall 142 that is arranged concentrically to and radially outside of the inner cylinder 14, wherein the cap 16 comprises an annular sealing lip 144 at an interior area of the cap 16, which is configured to sealingly abut against the sealing wall 142 when the cap 16 is mounted to the cream pot 12. On the one hand, a reliable sealing can be provided between the cap 16 and the cream pot 12. On the other hand, the piston 22 can be moved to its upper dead point in the inner cylinder 14 wherein restriction of the movement by the sealing lips 144 of the cap 16 can be avoided.

In order to fully empty the dispensing container 10, a cover area 146 of the cap 16 is curved axially inwardly towards the inner cylinder 14 of the cream pot 12 and an inner surface 148 of the cap 16 at the cover area 146 corresponds with an upper surface 150 of the piston 22. Preferably, the cover area 146 is curved axially inwardly towards the dispensing outlet 18. By providing a cover area 146 of the cap 16 with such a curvature, the upper surface 150 of the piston 22 almost fully abuts the inner surface 148 of the cap 16 at the cover area 146 when the piston 22 is at its upper dead point. Accordingly, the storage volume of the dispensing container 10 can be almost fully emptied.

As outlined above, a dispensing container 10 is provided that allows a predefined dosage of the viscous product stored in the storage volume and that has reduced leakage of the viscous product.

In the embodiment shown in FIGS. 1 to 20, the dispensing container 10 has been shown as a cream jar. However, it is also possible that the dispensing container has a pen-like structure and is configured as a so-called click-pen.

The invention claimed is:

1. A dispensing container (10) for viscous products comprising:
a cream pot (12) having an inner cylinder (14) that defines a storage volume configured to store a viscous product;
a cap (16) configured to close the cream pot (12) and having a dispensing outlet (18);
a screw rod (20) rotatably connected to the cream pot (12);
a piston (22) having an inner thread (24) and being coupled to the screw rod (20) such that rotation of the screw rod (20) leads to movement of the piston (22) in the inner cylinder along a longitudinal axis (26) of the screw rod (20) to reduce the storage volume of the inner cylinder (14) and to dispense the product through the dispensing outlet (18);
an indexing mechanism (28) is provided that is configured to lock the screw rod (20) in a plurality of rotational positions with respect to the cream pot (12), wherein the indexing mechanism (28) comprises indexing spring elements (30) located at the screw rod (20) and indexing sections (32) located at a bottom (48) of the cream pot (12), wherein the indexing spring elements (30) of the screw rod (20) are configured to interact with the indexing sections (32) of the cream pot (12) in order to lock the screw rod (20) with respect to the cream pot (12); and
an outer decorative shell base member (56), wherein the outer decorative shell base member (56) is configured to house the cream pot (12), wherein a bottom portion (64) of the outer decorative shell base member (56) comprises an actuating section (66) that is configured to actuate rotational movement of the screw rod (20) with respect to the cream pot (12) in an actuation direction.

2. The dispensing container (10) of claim 1, wherein the indexing mechanism (28) is synchronized with the lifting mechanism (46) such that the screw rod (20) is in the non-dispensing position when rotation of the screw rod (20) is locked with respect to the cream pot (12).

3. The dispensing container (10) of claim 1, an outside bottom portion (70) of the cream pot (12) comprises a mounting ring (84) having an annular undercut (86), wherein the outer decorative shell base member (56) comprises mounting features (88) having undercuts (90), wherein the undercut (86) of the mounting ring (84) interacts with the undercuts (90) of the mounting features (88) to fasten the cream pot (12) in the outer decorative shell base member (56).

4. The dispensing container (10) of claim 1, the outer decorative shell base member (56) comprises a base part (92) made from glass or metal and a function part (94) made from plastic connected to the base part (92), wherein the function part (94) comprises the actuating section (66), locking features (82) and mounting features (88).

5. The dispensing container (10) of claim 1, wherein the cream pot (12) comprises a plurality of guiding sections (116), which are arranged on an outer circumference (118) of the cream pot (12), wherein the cap (16) comprises a plurality of guiding bridges (120), wherein the guiding sections (116) are configured to guide the guiding bridges (120) into a predetermined position when the cap (16) is mounted to the cream pot (12).

6. The dispensing container (10) of claim 1, wherein a cover area (146) of the cap (16) is curved axially inwardly towards the inner cylinder (14) of the cream pot (12), wherein an inner surface (148) of the cap (16) at the cover area (146) corresponds with an upper surface (150) of the piston (22).

7. The dispensing container (10) of claim 1, wherein a gasket (132) is provided that is arranged between the screw rod (20) and the cream pot (12), wherein the gasket (132) is configured to prevent leakage between the screw rod (20) and the cream pot (12).

8. The dispensing container (10) of claim 1, wherein the screw rod (20) comprises a shaft (136) having an unthreaded section (138), wherein the piston (22) has an inner unthreaded section (140), wherein an outer diameter of the unthreaded section (138) of the shaft (136) is bigger than an inner diameter of the inner unthreaded section (140), such that a bearing seal is formed between the unthreaded section (138) of the shaft (136) and the inner unthreaded section (140) of the piston (22).

9. The dispensing container (10) of claim 1, wherein the cream pot (12) comprises an annular sealing wall (142) that is arranged concentrically to and radially outside of the inner cylinder (14), wherein the cap (16) comprises an annular sealing lip (144) at an interior area of the cap (16), which is configured to sealingly abut against the sealing wall (142) when the cap (16) is mounted to the cream pot (12).

10. The dispensing container (10) of claim 1, an outside bottom portion (70) of the cream pot (12) comprises an anti-rotation device (80), wherein the bottom portion (64) of the outer decorative shell base member (56) comprises locking features (82), wherein the anti-rotation device (80) is configured to interact with the locking features (82) so as to allow actuation of the screw rod (20) in the actuation direction and to hinder actuation of the screw rod (20) in a locking direction which is opposite the actuation direction.

11. The dispensing container (10) of claim 10, wherein an outside bottom portion (70) of the cream pot (12) comprises a mounting ring (84) having an annular undercut (86), wherein the outer decorative shell base member (56) comprises mounting features (88) having undercuts (90), wherein the undercut (86) of the mounting ring (84) interacts with the undercuts (90) of the mounting features (88) to fasten the cream pot (12) in the outer decorative shell base member (56).

12. The dispensing container (10) of claim 10, wherein the outer decorative shell base member (56) comprises a base part (92) made from glass or metal and a function part (94) made from plastic connected to the base part (92), wherein the function part (94) comprises the actuating section (66), the locking features (82) and the mounting features (88).

13. The dispensing container (10) of claim 1, wherein the container (10) comprises a lifting mechanism (46) that is configured to lift the screw rod (20) from the bottom (48) of the cream pot (12) between a non-dispensing position and a dispensing position upon rotation of the screw rod (20) with respect to the cream pot (12).

14. The dispensing container (10) of claim 13, wherein the lifting mechanism (46) comprises wave-like or step-like sliding surfaces (50) arranged at the screw rod (20) and deflection surfaces (52) arranged at the bottom (48) of the cream pot (12), wherein rotation of the screw rod (20) with respect to the cream pot (12) leads to a sliding movement of the wave-like or step-like sliding surfaces (50) on the deflection surfaces (52) such that the screw rod (20) is moved between the non-dispensing position and the dispensing position.

15. The dispensing container of claim 13, wherein the lifting mechanism (46) and a valve opening mechanism (100) are synchronized such that a valve (96) is in the closed position when the screw rod (20) is in the non-dispensing position and that the valve (96) is in the open position when the screw rod (20) is in the dispensing position.

16. The dispensing container (10) of claim 13, wherein the indexing mechanism (28) is synchronized with the lifting mechanism (46) such that the screw rod (20) is in the non-dispensing position when rotation of the screw rod (20) is locked with respect to the cream pot (12).

17. A dispensing container (10) for viscous products comprising:
   a cream pot (12) having an inner cylinder (14) that defines a storage volume configured to store a viscous product;
   a cap (16) configured to close the cream pot (12) and having a dispensing outlet (18);
   a screw rod (20) rotatably connected to the cream pot (12);
a piston (22) having an inner thread (24) and being coupled to the screw rod (20) such that rotation of the screw rod (20) leads to movement of the piston (22) in the inner cylinder along a longitudinal axis (26) of the screw rod (20) to reduce the storage volume of the inner cylinder (14) and to dispense the product through the dispensing outlet (18);
   an indexing mechanism (28) is provided that is configured to lock the screw rod (20) in a plurality of rotational positions with respect to the cream pot (12), wherein the indexing mechanism (28) comprises indexing spring elements (30) located at the screw rod (20) and indexing sections (32) located at a bottom (48) of the cream pot (12), wherein the indexing spring elements (30) of the screw rod (20) are configured to interact with the indexing sections (32) of the cream pot (12) in order to lock the screw rod (20) with respect to the cream pot (12); and
   a valve (96) is provided that is configured to close the dispensing outlet (18), wherein the valve (96) comprises a valve member (97), wherein a valve opening mechanism (100) is provided that is configured to move the valve member (97) along the longitudinal axis (26) of the screw rod (20) between a closed position in which the dispensing outlet (18) is closed by the valve member (97) and an open position in which the dispensing outlet (18) is open, wherein the screw rod (20) comprises valve actuating features (102), that are configured to rotate the valve member (97) about the longitudinal axis (26) of the screw rod (20) with respect to the cap (16), thereby actuating the valve opening mechanism (100).

18. The dispensing container (10) of claim 17, wherein the valve opening mechanism (100) comprises valve opening features (104) arranged at the cap (16) and wave-like or step-like valve lifting features (106) arranged at the valve member (97), wherein the valve opening features (104) and the valve lifting features (106) are configured to move the valve member (97) between the closed position and the open position upon rotation of the valve member (97) about the longitudinal axis (26) of the screw rod (20) with respect to the cap (16).

19. The dispensing container (10) of claim 17, wherein a spring member (98) is provided that is connected to the cap (16) and configured to preload the valve member (97) into the closed position.

\* \* \* \* \*